United States Patent [19]

Metz

[11] Patent Number: 4,980,498

[45] Date of Patent: Dec. 25, 1990

[54] METHOD OF PRODUCING 2-(2-HYDROXYETHOXY)-ETHANOL ESTER OF FLUFENAMIC ACID

[75] Inventor: Gunter Metz, Blaubeuren, Fed. Rep. of Germany

[73] Assignee: Merckle GmbH, Fed. Rep. of Germany

[21] Appl. No.: 331,125

[22] Filed: Mar. 31, 1989

[30] Foreign Application Priority Data

Mar. 31, 1988 [DE] Fed. Rep. of Germany ....... 3811119

[51] Int. Cl.$^5$ ........................................... C07C 229/00
[52] U.S. Cl. ..................................................... 560/47
[58] Field of Search ........................................... 560/47

[56] References Cited

U.S. PATENT DOCUMENTS

| | | | |
|---|---|---|---|
| 3,692,818 | 9/1972 | Boltze et al. | 560/47 |
| 3,694,489 | 9/1972 | Boltze et al. | 560/47 |
| 4,198,431 | 4/1980 | Kato | 560/47 |

FOREIGN PATENT DOCUMENTS

| | | | |
|---|---|---|---|
| 726767 | 1/1966 | Canada | 560/47 |
| 904340 | 7/1972 | Canada | 560/47 |
| 1939112 | 2/1971 | Fed. Rep. of Germany | 560/47 |
| 54-3032 | 1/1979 | Japan | 560/47 |
| 58-148840 | 9/1983 | Japan | 560/47 |
| 59-181245 | 10/1984 | Japan | 560/47 |

*Primary Examiner*—Bruce Gray
*Attorney, Agent, or Firm*—Venable, Baetjer, Howard & Civiletti

[57] ABSTRACT

By using a new method 2-(2-hydroxyethoxy)-ethanol ester is produced from flufenamic acid as a result of direct esterification with diol with an excess of 8–15 mol diol per mol flufenamic acid without concurrent removal of water.

22 Claims, No Drawings

METHOD OF PRODUCING 2-(2-HYDROXYETHOXY)-ETHANOL ESTER OF FLUFENAMIC ACID

The present invention relates to a new, improved method of producing the well-known 2-(2-hydroxyethoxy)- ethyl-N-(α,α,α-trifluoro-m-tolyl)-anthranilate (I), i.e., 2-(2-hydroxyethoxy)ethanol ester of flufenamic acid).

From the West German patent DE-PS 19 39 112 it is known that (I) may be produced by converting the potassium salt of N-(α,α,α-trifluoro-m-tolyl)anthranilic acid (II) (flufenamic acid) with 2-(2-chloroethoxy)ethanol in dimethylformamide. However, this method is unsatisfactory when applied on a technical scale and has substantial drawbacks concerning synthesis, processing and purity of the end product.

A method which circumvents these drawbacks is described in the West German patent DE-PS 28 34 167 in which (II) is directly converted by using an excess of 2-(2-hydroxyethoxy)ethanol (III) in inert solvents or in the absence of solvent by acidic catalysis. The water produced during the esterification is thereby azeotropically removed. Subsequently, according to the method, the excess of (III) is distilled off in vacuum, the residue absorbed in diisopropyl ether and washed with caustic soda, water or a saline solution, evaporated again in vacuum, whereupon the ester (I) is subjected to molecular distillation. In accordance with this method a reaction time of 16 hours at 140 degrees Celsius, which included the use of p-toluol sulfonic acid as a catalyst, yields approximately 69% (I). By using sulfuric acid as a catalyst, a 10-hour reaction time at 140 degrees Celsius yielded approximately 36% (I).

By using an alternative production method according to the West German patent DE-PS 28 34 168, flufenamic acid (II) is initially esterified with a $C_1$-$C_5$-alcohol by azeotropical elimination of the produced water. The forming low molecular weight ester is then esterified in interchange with 2-(2-hydroxyethoxy)ethanol (III).

Surprisingly, it has now been found, that the acidically catalyzed direct esterification of the acid (II) can be obtained with diol (III) without azeotropical removal of reaction water, with significantly shorter reaction times and even at lower temperatures with purified (I) yields of 60-70% (crude product 80-90%) if a substantial excess of diol (III) is employed.

It is especially surprising, in this context, that the remaining reaction water in the preparation allows for such a high yield of ester, since according to prior art, e.g., West German patent DE-PS 28 34 167, a shift in the reaction equilibrium in the favor of ester requires removal of the reaction water, i.e., azeotropical removal.

The method described in the invention for producing 2-(2-hydroxyethoxy)ethanol ester of flufenamic acid (N- (α,α,α-trifluoro-m-tolyl)anthranilic acid) by using direct esterification of flufenamic acid and an excess of 2-(2-hydroxyethoxy)ethanol at a reaction temperature of 100 to 140 degrees Celsius, preferably 100 to 125 degrees Celsius and especially preferably 100 to 120 Celsius, in the presence of acidic catalysts is characterized by the fact, that the conversion occurs with an excess of 8-15 moles of diol per mole flufenamic acid without concurrent removal of the reaction water from the reaction preparation.

The method described in the invention occurs in the presence of acidic catalysts, such as Lewis acids, zinc chloride, sulfuric acid, phosphoric acid, benzol sulfonic acid, p-toluol sulfonic acid, especially p-toluol sulfonic acid monohydrate or mixtures of phosphoric acid and p-toluol sulfonic acid, at molecular conditions of 0.25 to 1 mole, preferably 0.5 to 1 mole catalyst per mole acid (II). Preferable sulfuric acid or p-toluol sulfonic acid is used. The reaction temperature should preferably be 100 to 125 degrees Celsius and especially preferred is 100 to 120 degrees Celsius.

Higher temperatures generally do not increase the yield. However, during mixing of catalysts of phosphoric acid and p-toluol sulfonic acid at 140 degrees Celsius was an increase of ester yield of around 5-20% noticed. By using a mixture of phosphoric acid and p-toluol sulfonic acid, quantities of added catalyst should preferably be between 0.5 and 1 mole. In this case, an increase of reaction time to 8 hours may be necessary, if a reaction temperature of 120 degrees Celsius is chosen. The reaction time is 2 to 4 hours for each mole acid (II), when using 0.5 to 1 mole catalyst, especially with sulfuric acid or p-toluol sulfonic acid, and only for catalyst quantities less than 0.5 mole per mole acid (II) should it be increased to 6, maximum 8 hours. Reaction times up to 6 hours are preferred.

For each 1 mole of acid (II) used, 8 to 15 mol, preferably 10.5 to 12 mol, diol (III) is added.

According to the method of the invention, the excess of diol (III) is advantageously removed from the reaction preparation without distillation. This is done either through (A) neutralization or light alkalization of the preparation with aqueous solutions of alkali or alkaline earth hydroxides or carbonates, during which the crude ester (I) is separated and excess diol is transferred to the aqueous phase, or (B) stirring the reaction preparation, preferably at a temperature of 20-60 degrees Celsius with solid alkali or alkaline earth hydroxide or carbonate and direct extraction of the crude ester (I) with carbonic hydrogen substances, such as Toluol.

The crude ester (I) obtained may directly be added to a two-phase high vacuum distillation, during which the first phase solvent residuals are removed and during the second phase, the purified ester (I) is separated through distillation from higher molecular weight pollutants, especially diester produced during the reaction and thermically, during distillation. A further, very gentle, processing method consists of purifying the crude ester (I) without distillation, using preparative median pressure fluid chromatography and applying a pressure of 10-20 bar, adding the usual adsorbents, particularly silica gel.

EXAMPLE 1

10 mol N-(α,α,α-trifluoro-m-tolyl)anthranilic acid (II) were suspended in 120 mol 2-(2-hydroxyethoxy)-ethanol (III) and mixed with 5 moles of concentrated sulfuric acid with stirring. The preparation was then heated for three hours at 120 degrees Celsius. After cooling off to room temperature the preparation was neutralized with a sodium carbonate solution (754 g sodium carbonate dissolved in 15 liters of water) and stirred for 15 more minutes. The separated crude ester was diluted with 1 liter chloroform, then separated and the aqueous solution was twice more extracted with 1 liter of chloroform.

The combined chloroform phases were washed with 2 liters of water, dried over sodium sulphate, filtered and evaporated in vacuum. The obtained crude ester was distilled in a two-phase, high vacuum distillation, removing during the first phase, at 100 degrees Celsius and 1.333 Pa ($10^{-2}$ torr), solvent residuals and, in the second phase, overdistilling the clean ester, at 140 degrees Celsius and 9.33 Pa ($7\times10^{-3}$ torr). Yield 2.563 g (69.4%).

The same procedure with 5 hours reaction time and 110 degrees Celsius reaction temperature, yielded 65.2% of ester.

EXAMPLE 2

1 mole N-($\alpha,\alpha,\alpha$-trifluoro-m-tolyl)anthranilic acid (II) was suspended together with 1 mole p-toluol sulfonic acid monohydrate in 10.5 mole 2-(2-hydroxyethoxy)ethanol (III) and heated for three hours at 120 degrees Celsius with stirring under nitrogen. After cooling off, the preparation was adjusted to pH 8 by adding a saturated sodium carbonate solution and then continuing stirring for 15 minutes. The preparation was twice extracted with 250 ml chloroform and the chloroform phase washed with water and dried over sodium sulphate. After evaporation of the chloroform, the obtained crude ester was subjected to a two-phase, high vacuum distillation. Yield 68.6%.

EXAMPLE 3

(a) 1 mole N-($\alpha,\alpha,\alpha$-trifluoro-m-tolyl)anthranilic acid (II) was suspended in 8 moles 2-(2-hydroxyethoxy)ethanol (III) and after adding 0.18 mole p-toluol sulfonic acid monohydrate and 0.23 mole o-phosphoric acid (85%-ish) was heated for 6 hours at 120 degrees Celsius. After cooling off to 60 degrees Centigrade, the preparation, by portions, was mixed with 75 g potassium carbonate and continuedly stirred for 30 minutes at 60 degrees Celsius. After cooling off to room temperature, the preparation was twice extracted using 250 ml of toluol. The toluol phase, washed with water, was evaporated in vacuum and the residue subjected to a two-phase high vacuum distillation. Yield 40%.

(b) Example (a) was repeated at a temperature of 140 degrees Celsius. After a reaction time of 6 hours, a yield of 63.2% was obtained.

(c) Example (a) was repeated with 0.27 mole toluol sulfonic acid and 0.35 mole phosphoric acid with a reaction time of 8 hours and a temperature of 120 degrees Celsius. A yield of 56% ester was thereby obtained.

EXAMPLE 4

32 g crude ester (I), produced from 0.1 mole (II) according to the method used in Example 1, was dissolved in 50 ml of a mixture of toluol and methanol (95:5). This solution was eluted in a glass column filled with silica gel 60 (grain size 0.04–0.63 mm), 46 cm long and a diameter of 4.9 cm, at a pressure of 10–20 bar, with the same solvent. After the separation of a small precursor, containing mainly diester, the eluate was evaporated in vacuum, thereby obtaining 25.9 g purified ester (I), corresponding to a total yield of 70.2%.

What is claimed is:

1. A method of producing 2-(2-hydroxyethoxy)ethanol ester of flufenamic acid which comprises
    (a) directly esterifying flufenamic acid with an excess of 2-(2-hydroxyethoxy)ethanol at a reaction temperature of 100 to 140 degrees Celsius, in the presence of acid catalysts without concurrently removing the reaction water from the reaction mixture, wherein the mol ratio of flufenamic acid to 2-(2-hydroxyethoxy)ethanol is from about 1:8 to about 1:15;
    (b) removing excess diol from the reaction mixture by neutralizing or alkalization with an aqueous solution of an alkali or alkaline earth hydroxide or carbonate, followed by transferring excess diol to the aqueous phase or direct extraction with an organic solvent; and
    (c) purifying the crude ester by vacuum distillation or pressure fluid chromatography.

2. The method of claim 1, wherein 0.25 to 1 mol catalyst per mole acid is employed.

3. The method of claim 1, wherein the mol ratio of acid to 2-(2-hydroxyethoxy)ethanol is about: 1:10.5 to 12.

4. The method of claim 2, wherein the mol ratio of acid to 2-(2-hydroxyethoxy)ethanol is about: 1:10.5 to 12.

5. The method of claim 1 wherein the catalyst is a p-toluol sulfonic acid monohydrate.

6. The method of claim 1 wherein, subsequent to reaction an aqueous solution of alkali or alkaline earth hydroxide is added to the reaction mixture in order to remove excess diol upon completion of the esterification process, and the crude ester product is separated from the excess 2-(2-hydroxyethoxy)ethanol in the aqueous phase.

7. The method of claim 2 wherein an aqueous solution of alkali or alkaline earth hydroxide is added to the reaction mixture in order to remove excess diol upon completion of the esterification process, and the crude ester product is separated from the excess 2-(2-hydroxyethoxy)ethanol in the aqueous phase.

8. The method of claim 3 wherein an aqueous solution of alkali or alkaline earth hydroxide is added to the reaction mixture in order to remove excess diol upon completion of the esterification process, and the crude ester product is separated from the excess 2-(2-hydroxyethoxy)ethanol in the aqueous phase.

9. The method of claim 4 wherein an aqueous solution of alkali or alkaline earth hydroxide is added to the reaction mixture in order to remove excess diol upon completion of the esterification process, and the crude ester product is separated from the excess 2-(2-hydroxyethoxy)ethanol in the aqueous phase.

10. The method of claim 5 wherein an aqueous solution of alkali or alkaline earth hydroxide is added to the reaction mixture in order to remove excess diol upon completion of the esterification process, and the crude ester product is separated from the excess 2-(2-hydroxyethoxy)ethanol in the aqueous phase.

11. The method of claim 1, wherein the reaction mixture is mixed with solid alkali or alkaline earth hydroxide or carbonate until neutralization in order to remove excess diol and the crude ester is extracted with a hydrocarbon solvent.

12. The method of claim 2, wherein the reaction mixture is mixed with solid alkali or alkaline earth hydroxide or carbonate until neutralization in order to remove excess diol and the crude ester is extracted with a hydrocarbon solvent.

13. The method of claim 3, wherein the reaction mixture is mixed with solid alkali or alkaline earth hydroxide or carbonate until neutralization in order to remove excess diol and the crude ester is extracted with a hydrocarbon solvent.

14. The method of claim 4, wherein the reaction mixture is mixed with solid alkali or alkaline earth hydroxide or carbonate until neutralization in order to remove excess diol and the crude ester is extracted with a hydrocarbon solvent.

15. The method of claim 5, wherein the reaction mixture is mixed with solid alkali or alkaline earth hydroxide or carbonate until neutralization in order to remove excess diol and the crude ester is extracted with a hydrocarbon solvent.

16. The method of claim 11, wherein said hydrocarbon solvent is toluol.

17. The method of claim 1, wherein the crude ester product is purified by median-pressure liquid chromatography at pressures of 10–20 bar.

18. The method of claim 2, wherein the crude ester product is purified by median-pressure liquid chromatography at pressures of 10–20 bar.

19. The method of claim 3, wherein the crude ester product is purified by median-pressure liquid chromatography at pressures of 10–20 bar.

20. The method of claim 4, wherein the crude ester product is purified by median-pressure liquid chromatography at pressures of 10–20 bar.

21. The method of claim 5, wherein the crude ester product is purified by median-pressure liquid chromatography at pressures of 10–20 bar.

22. The method of claim 17 wherein silica gel is used as the adsorbent in said chromatography.

* * * * *